(12) United States Patent
Blanda et al.

(10) Patent No.: US 8,785,394 B2
(45) Date of Patent: Jul. 22, 2014

(54) SUSTAINED ACTION FORMULATION OF CYCLOSPORIN FORM 2

(71) Applicant: Allergan, Inc., Irvine, CA (US)

(72) Inventors: Wendy M. Blanda, Tustin, CA (US); Mayssa Attar, Placentia, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/676,551

(22) Filed: Nov. 14, 2012

(65) Prior Publication Data

US 2013/0123195 A1    May 16, 2013

Related U.S. Application Data

(60) Provisional application No. 61/559,838, filed on Nov. 15, 2011, provisional application No. 61/563,199, filed on Nov. 23, 2011.

(51) Int. Cl.
| *A61K 38/13* | (2006.01) |
| *A61P 27/02* | (2006.01) |
| *C07K 7/64* | (2006.01) |
| *C07K 1/30* | (2006.01) |
| *A61K 9/00* | (2006.01) |

(52) U.S. Cl.
CPC ............... *A61K 38/13* (2013.01); *C07K 7/645* (2013.01); *C07K 1/306* (2013.01); *A61K 9/0048* (2013.01)
USPC ........................ 514/20.5; 530/321; 530/317

(58) Field of Classification Search
CPC ..... A61K 38/13; A61K 9/0048; A61K 47/36; C07K 7/645; C07K 1/306
See application file for complete search history.

(56) References Cited

U.S. PATENT DOCUMENTS

| 5,294,604 | A | * | 3/1994 | Nussenblatt et al. | ......... 424/450 |
| 2001/0041671 | A1 | * | 11/2001 | Napoli | ............................... 514/9 |
| 2005/0192264 | A1 | * | 9/2005 | Penfold | ......................... 514/179 |
| 2006/0205639 | A1 | | 9/2006 | Domb et al. | |
| 2008/0299206 | A1 | | 12/2008 | Lee et al. | |
| 2013/0023482 | A1 | * | 1/2013 | Gore et al. | ................... 514/20.5 |

FOREIGN PATENT DOCUMENTS

| GB | 2211848 | 7/1989 |
| WO | WO 89-01772 | 3/1989 |
| WO | WO 2005-072701 | 8/2005 |
| WO | WO 2012-166610 | 12/2012 |

OTHER PUBLICATIONS

International Search Report—PCT/US2012/064985 received Feb. 21, 2013.
International Search Report—PCT/US2012/064998, received Jan. 24, 2013.
Bowen P., "Particle Size Distribution Measurement from Millimeters to Nanometers and from Rods to Platelets", Journal of Dispersion Science and Technology, vol. 23, No. 5, Jan. 1, 2002, pp. 631-662.
International Search Report—PCT/US2012/064998, received Feb. 6, 2013.
International Search Report—PCT/US2012/065011, received Feb. 6, 2013.

* cited by examiner

*Primary Examiner* — Julie Ha
*Assistant Examiner* — Li Ni Komatsu
(74) *Attorney, Agent, or Firm* — Laura L. Wine; Joel B. German; Debra D. Condino (57) ABSTRACT

Disclosed herein are methods of treating diseases of the eye by administering to the subconjunctival space a formulation comprising cyclosporin A form 2 and a hydrogel.

2 Claims, 8 Drawing Sheets

SUSTAINED ACTION FORMULATION OF CYCLOSPORIN FORM 2

CROSS-REFERENCE TO RELATED APPLICATIONS

This patent application claims priority to U.S. Provisional Patent Application No. 61/559,838, filed Nov. 15, 2011, and U.S. Provisional Patent Application No. 61/563,199, filed Nov. 23, 2011, the entire contents of both of which are hereby incorporated by reference.

BACKGROUND

Cyclosporin A is the active ingredient in RESTASIS®, a topical ocular formulation approved in the United States for the treatment of dry eye. Topical cyclosporin is also used in the management of other ophthalmic conditions such as restoration of corneal sensitivity following refractive surgery, conjunctival and corneal inflammation, keratoconjuntivitis, graft versus host disease, post-transplant glaucoma, corneal transplants, mycotic keratitis, meibomian gland dysfunction, Thygeson's superficial punctate keratitis, uveitis, and Theodore's superior limbic keratoconjunctivitis.

Patient compliance is extremely important but many patients fail to comply with ocular medications. Moreover, some treatments for conditions other than dry eye dose more frequently than the twice-a-day dosing approved for RESTASIS®, and concentrations of cyclosporin A higher in tissue than RESTASIS® can deliver after multiple dosing would be beneficial to certain patients with severe conditions, such as graft vs. host disease. Some ocular diseases may require long-term therapy. For example, the National Eye Institute (NEI) has completed a study to evaluate 1 and 2 mg biodegradable implants of cyclosporin to treat uveitis. The NEI is also studying the use of non-degradable cyclosporin implants for treatment of graft vs. host disease. However, it should be noted that removing non-degradable implants after the dose has been depleted requires a second surgery. Some other relevant studies also have been conducted by the NEI or are in the process of recruiting patients for studies. Results for these NEI studies have not been published.

A single implantation or injection, which delivers high levels of cyclosporin constantly over a long period (weeks or months) is desirable. The use of multi-month biodegradable or bioerodible delivery system, which delivers cyclosporin to targeted anterior ocular tissues—at equal or greater concentration as RESTASIS®—is clearly desirable. It is also desirable to have an injectable formulation, which would avoid surgery. A formulation which could pass through a 22 gauge needle (or smaller) and avoid the ocular tissue damage which may occur with trocars, larger needles, or surgical implantation, is also desirable.

The reported success of injecting cyclosporin formulations into the conjunctiva for long-duration therapy has been highly limited: while short-term efficacy has been shown with some microspheres and other formulations, no formulation has been demonstrated to be equivalent or superior in delivering cyclosporin to anterior tissue, when compared to RESTASIS® for a period of at least 3 months.

Biodegradable implants, which can be delivered through a 22 gauge needle, do not deliver sufficient drug over a sufficient period of time to meet the need. Biodegradable gel-forming suspensions perform better but, still do not meet the need.

The inventors have surprisingly found that the formulations of the invention, when delivered to the subconjunctival space of the eye through a 22 or smaller gauge needle, deliver cyclosporin A to most anterior ocular tissue for a sustained period of time.

DETAILED DESCRIPTION

Cyclosporin A

Cyclosporin A (CsA) is a cyclic peptide having the following chemical structure:

Its chemical name is cyclo[[(E)-(2S,3R,4R)-3-hydroxy-4-methyl-2-(methylamino)-6-octenoyl]-L-2-aminobutyryl-N-methylglycyl-N-methyl-L-leucyl-L-valyl-N-methyl-L-leucyl-L-alanyl-D-alanyl-N-methyl-L-leucyl-N-methyl-L-leucyl-Nmethyl-L-valyl]. It is also known by the names cyclosporine, cyclosporine A, ciclosporin, and ciclosporin A. It is the active ingredient in RESTASIS® (Allergan, Inc., Irvine, Calif.), an emulsion comprising 0.05% (w/v)

cyclosporin. RESTASIS® is approved in the United States to increase tear production in patients whose tear production is presumed to be suppressed due to ocular inflammation associated with keratoconjunctivitis sicca.

Cyclosporin A Form 2

Cyclosporin A is known to exist in an amorphous form, liquid crystal form, tetragonal crystalline form (form 1), and an orthorhombic form (form 3). A new crystalline form, cyclosporin A form 2, has recently been discovered.

Figure 1:
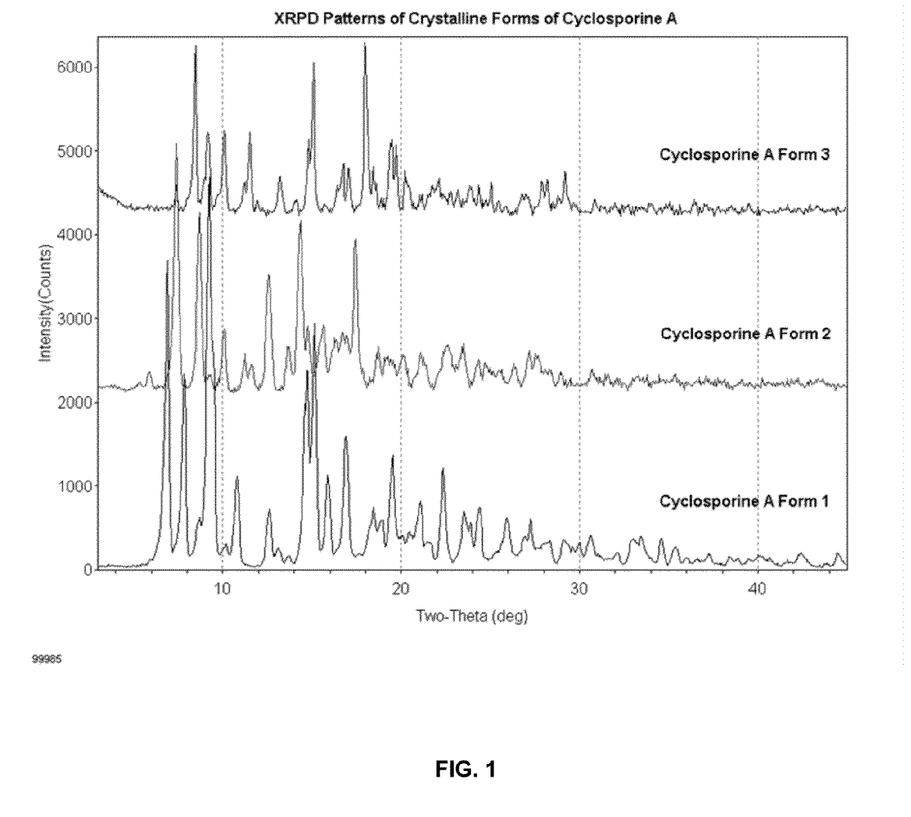
FIG. 1 depicts characteristic X-ray powder diffraction (XRPD) patterns of CsA in a new crystalline form (designated as Form 2 herein), tetragonal form (designated as Form 1 herein), and orthorhombic form (designated as Form 3 herein).
Figure 2:
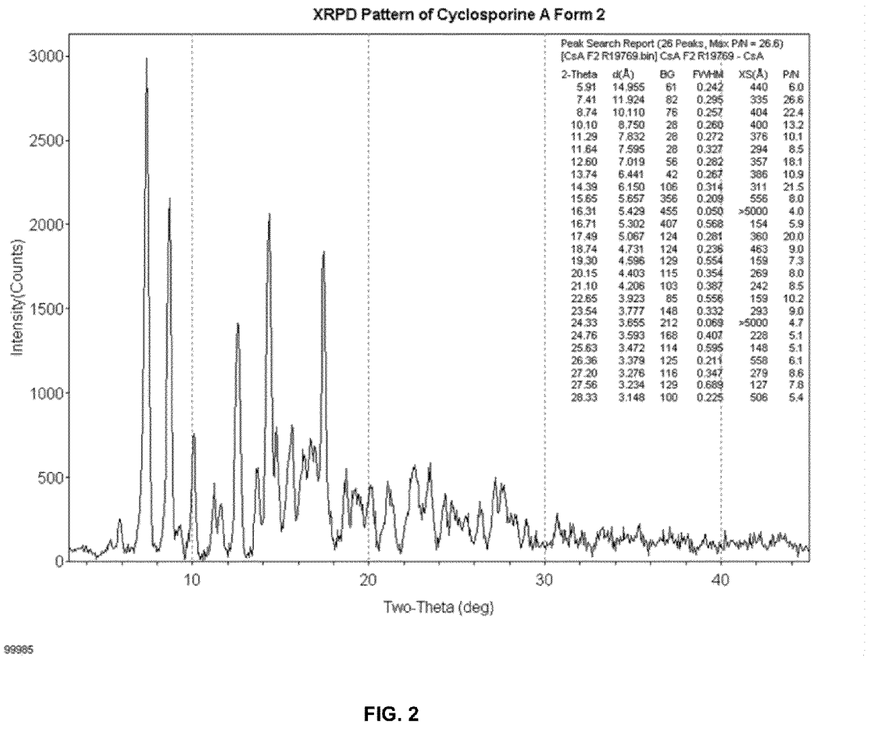
FIG. 2 depicts the XRPD diffractogram of CsA crystalline Form 2.

The XRPD pattern of CsA Form 2 differs significantly from the tetragonal form and orthorhombic form (FIG. 1). The major crystalline peaks for CsA form 2 appear at (2θ) when scanned by an X-ray diffractometer with X-ray source as Cu Kα radiation, λ=1.54 Å, at 30 kV/15 mA: 7.5, 8.8, 10.2, 11.3, 12.7, 13.8, 14.5, 15.6 and 17.5 (d-spacing in crystal lattice at about 11.8, 10.0, 8.7, 7.8, 7.0, 6.4, 6.1, 5.6 and 5.1 Å, respectively, FIG. 2). These major peaks are defined as those being unique to Form 2 relative to the orthorhombic or tetragonal forms; as well as, peaks having an intensity greater than 5 times the background.

In one embodiment, the new crystalline form (Form 2) of CsA is a nonstoichiometric hydrate of Cyclosporin A. In another embodiment, the crystalline Form 2 is represented by the formula:

X H$_2$O, wherein X is the number of molecules of water and varies from 0 to 3. In one embodiment, X in the above formula is 2.

Form 2 appears to be a kinetically stable form of CsA in aqueous suspensions. Suspensions containing Form 2 show no conversion to other known polymorphic or pseudomorphic forms upon storage. It has been found that Form 1 and the amorphous form convert to Form 2 in the presence of water.

The single crystal structure of the hydrate form of CsA Form 2 has been determined and the crystal structure parameters are listed in Table 2. These results indicate that Form 2 is unique compared to other known crystalline forms of cyclosporine A.

TABLE 1

Crystal data and data collection parameters of crystal structure solution of CsA Form 2.

| formula | $C_{62}H_{115}N_{11}O_{14}$ |
|---|---|
| formula weight | 1238.67 |
| space group | $P\,2_1\,2_1\,2_1$ (No. 19) |
| a (Å) | 12.6390(5) |
| b (Å) | 19.7582(8) |
| c (Å) | 29.568(2) |
| volume (Å$^3$) | 7383.8(7) |
| Z | 4 |
| $d_{calc}$ (g cm$^{-3}$) | 1.114 |
| crystal dimensions (mm) | 0.27 × 0.18 × 0.12 |
| temperature (K) | 150 |
| radiation (wavelength in Å) | Cu K$_3$(1.54184) |
| monochromator | confocal optics |
| linear abs coef (mm$^{-1}$) | 0.640 |
| absorption correction applied | empirical$^a$ |
| transmission factors (min, max) | 0.80, 0.93 |
| diffractometer | Rigaku RAPID-II |
| h, k, l range | −13 to 13 −21 to 21 −32 to 21 |
| 2θ range (deg) | 5.38-115.00 |
| mosaicity (deg) | 1.31 |
| programs used | SHELXTL |
| F$_{000}$ | 2704.0 |
| weighting | $1/[\sigma^2(Fo^2) + (0.0845P)^2 + 0.0000P]$ |

TABLE 1-continued

Crystal data and data collection parameters of crystal structure solution of CsA Form 2.

| | where P = (Fo$^2$+ 2Fc$^2$)/3 |
|---|---|
| data collected | 37360 |
| unique data | 9964 |
| R$_{int}$ | 0.077 |
| data used in refinement | 9964 |
| cutoff used in R-factor calculations | F$_o^2$ > 2.0s(F$_o^2$) |
| data with I > 2.0s(I) | 6597 |
| number of variables | 834 |
| largest shift/esd in final cycle | 0.00 |
| R(F$_o$) | 0.061 |

TABLE 1-continued

Crystal data and data collection parameters of crystal structure solution of CsA Form 2.

| | |
|---|---|
| $R_w(F_o^2)$ | 0.145 |
| goodness of fit | 1.037 |
| absolute structure determination | Flack parameter[b](0.0(3)) |

Figure 8:
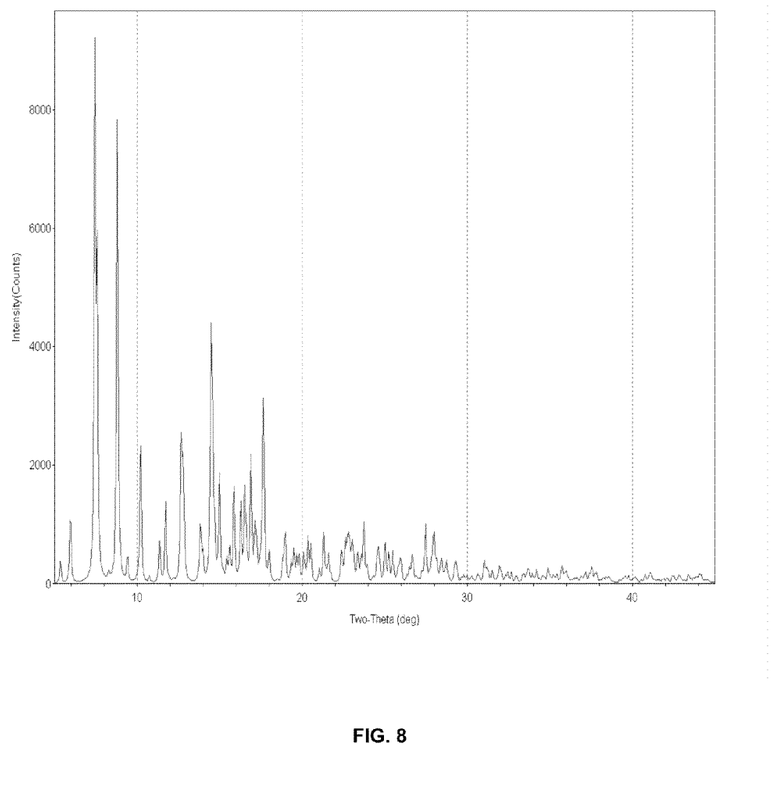
FIG. 8 shows the simulated XRPD pattern of cyclosporine A forms.

The asymmetric unit of this CsA Form 2 contains one cyclosporine A molecule and two water molecules. It is possible that any small molecule that can hydrogen bond to water could play the role of space filler, which would give a range of potential structures running from the orthorhombic dihydrate to distorted monoclinic dihydrate The XRPD pattern calculated from the single-crystal structure is shown in FIG. 8 and it matches the experimental pattern shown in FIG. 2. These matching patterns further corroborate that Form 2 is a unique and pure crystalline form of cyclosporine A.

Figure 3:
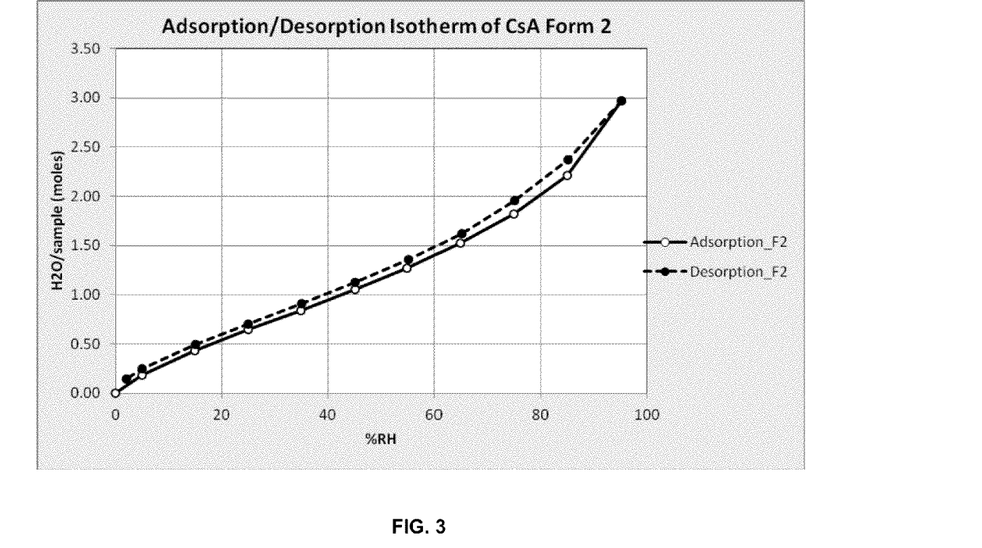
FIG. 3 depicts the water sorption/desorption profile of CsA Form 2.
Figure 4:
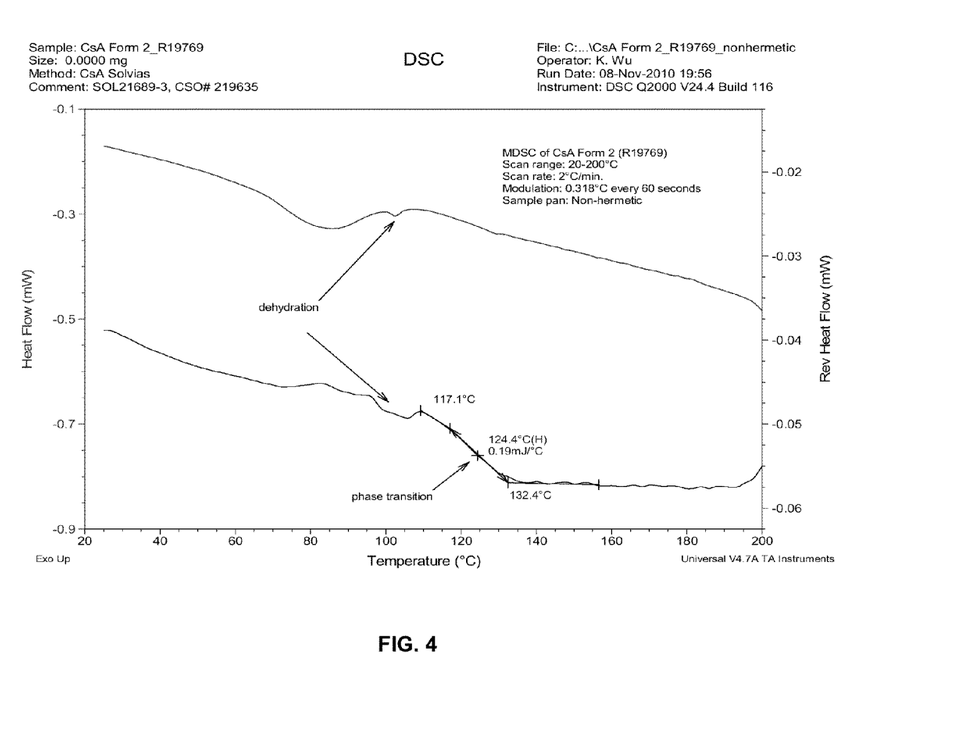
FIG. 4 depicts MDSC analysis of CsA Form 2 recovered from 0.04% formulation with 1% PS80.

Without wishing to be bound by theory, thermogravimetric analysis combined with KF titration and vapor sorption desorption analysis (VSA) suggest that CsA Form 2 is a non-stoichiometric hydrate of CsA. The vapor sorption analysis of Cyclosporine Form 2 indicates that water content in the new crystal form reversibly varies with relative humidity as shown in FIG. 3. Similar to the tetragonal form, the new CsA form undergoes a phase transition to a liquid crystal or amorphous form at 124.4° C. prior to melting as indicated by the modulated differential calorimetric (MDSC) analysis (FIG. 4).

Cyclosporin A Form 2 may be obtained by suspending amorphous 0.05% cyclosporin A (w/v) in 1% Polysorbate 80, heating the solution to 65° C., holding it at that temperature for 24 hours, and then recovering the precipitate by vacuum filtration. One can then use the cyclosporin A Form 2 thus obtained to generate additional amounts, using Cyclosporin A Form 2 as a seed crystal; in this method, one suspends about 30 g cyclosporin A in a solution of 900 ml water containing 1% (w/v) Polysorbate 80, heats the solution to 65° C., and then seeds it with 0.2 g of cyclosporin A Form 2 at a temperature of 52° C. The solution is then stirred for about 22 hours at a temperature of between about 61° C. and 65° C., and then recovers the precipitate that results.

Further details regarding CsA Form 2 may be found in U.S. patent application Ser. No. 13/480,710, the entire contents of which are incorporated by reference herein.

Sustained Action Formulations of Cyclosporin a Form 2

Compositions of the invention are ophthalmically acceptable formulations of Cyclosporin A form 2. By "ophthalmically acceptable," the inventors mean that the suspensions are formulated in such a way as to be non-irritating when administered to the eye of a mammal, such as a human.

The formulations of the invention comprise cyclosporin A form 2 and a hydrogel such as hyaluronic acid, hydroxypropyl cellulose, hydroxypropylmethyl cellulose, hydroxyethylcellulose, polyvinyl pyrolidone, and carboxymethylcellulose.

In one embodiment, the formulation comprises cyclosporin A form 2 at a concentration of about 0.001% to about 10% (w/v). In one embodiment, the suspension comprises cyclosporin A form 2 at a concentration of about 0.001% (w/v) to about 0.01%, about 0.001% (w/v) to about 0.04% (w/v), about 0.001% (w/v) to about 0.03% (w/v), about 0.001% (w/v) to about 0.02% (w/v), or about 0.001% (w/v) to about 0.01% (w/v). In another embodiment, the suspension comprises cyclosporin A form 2 at a concentration of about 0.01% (w/v) to about 0.05%, about 0.01% (w/v) to about 0.04% (w/v), about 0.01% (w/v) to about 0.03% (w/v), about 0.01% (w/v) to about 0.02% (w/v), or about 0.01% (w/v) to about 0.01% (w/v). In another embodiment, the suspension comprises cyclosporin A form 2 at a concentration of about 0.01% (w/v) to about 0.1%, about 0.1% (w/v) to about 0.5% (w/v), about 0.01% (w/v) to about 1% (w/v), or about 1% (w/v) to about 10%.

For example, the formulations may comprise about 0.001% (w/v), about 0.002% (w/v), about 0.003% (w/v), about 0.004% (w/v), about 0.005% (w/v), about 0.006% (w/v), about 0.007% (w/v), about 0.008% (w/v), about 0.009% (w/v), about 0.01% (w/v), about 0.015% (w/v), about 0.02% (w/v), about 0.025% (w/v), about 0.03% (w/v), about 0.035% (w/v), about 0.04% (w/v), about 0.045% (w/v), about 0.05% (w/v), about 0.055% (w/v), about 0.06% (w/v), about 0.065% (w/v), about 0.07% (w/v), about 0.075% (w/v), about 0.08% (w/v), about 0.085% (w/v), about 0.09% (w/v), about 0.095% (w/v), about 0.1% (w/v), about 0.15% (w/v), about 0.2% (w/v), about 0.25% (w/v), about 0.3% (w/v), about 0.35% (w/v), about 0.4% (w/v), about 0.45% (w/v), about 0.5% (w/v), about 0.55% (w/v), about 0.6% (w/v), about 0.65% (w/v), about 0.7% (w/v), about 0.75% (w/v), about 0.8% (w/v), about 0.85% (w/v), about 0.9% (w/v), about 0.95% (w/v), or about 1.0% (w/v) cyclosporin A form 2.

Methods of Treatment

Formulations of the invention may be used to treat any condition of the eye which is known to be amenable to topical treatment with cyclosporin A (such as with RESTASIS®) at the concentrations stated here. For example, compositions of the invention may be used to treat patients suffering from dry eye, to treat blepharitis and meibomian gland disease, to restore corneal sensitivity that has been impaired due to refractive surgery on the eye, to treat allergic conjunctivitis and atopic and vernal keratoconjunctivitis, and to treat ptyregia, conjunctival and corneal inflammation, keratoconjuntivitis, graft versus host disease, post-transplant glaucoma, corneal transplants, mycotic keratitis, Thygeson's superficial punctate keratitis, uveitis, and Theodore's superior limbic keratoconjunctivitis, among other conditions.

The International Dry Eye Workshop (DEWS) defines dry eye as "a multifactorial disease of the tears and ocular surface that results in symptoms of discomfort, visual disturbance, and tear film instability with potential damage to the ocular surface, accompanied by increased osmolarity of the tear film and inflammation of the ocular surface." It includes those conditions, such as keratoconjunctivitis sicca, that are caused by tear deficiency or excessive evaporation of tears.

Blepharitis is a chronic disorder producing inflammation of the anterior and posterior lid margin, with involvement of skin and its related structures (hairs and sebaceous glands), the mucocutaneous junction, and the meibomian glands. It can also affect the conjunctiva, tear film, and the corneal surface in advanced stages and may be associated with dry eye. Blepharitis is commonly classified into anterior or posterior blepharitis, with anterior affecting the lash bearing region of the lids, and posterior primarily affecting the meibomian gland orifices.

Meibomian gland disease most often occurs as one of three forms: primary meibomitis, secondary meibomitis, and meibomian seborrhea. Meibomian seborrhea is characterized by excessive meibomian secretion in the absence of inflammation (hypersecretory meibomian gland disease). Primary meibomitis, by contrast, is distinguished by stagnant and inspissated meibomian secretions (obstructive hypersecretory meibomian gland disease). Secondary meibomitis represents a localized inflammatory response in which the meibomian glands are secondarily inflamed in a spotty fashion from an anterior lid margin blepharitis.

Impaired corneal sensitivity often occurs after refractive surgery, such as photorefractive keratectomy, laser assisted sub-epithelium keratomileusis (LASEK), EPI-LASEK, customized transepithelial non-contact ablation, or other procedures in which the corneal nerves are severed. Impaired corneal sensitivity may also occur after viral infection, such as by HSV-1, HSV-2, and VZV viruses. Patients with impaired corneal sensitivity often complain that their eyes feel dry, even though tear production and evaporation may be normal, suggesting that "dryness" in such patients is actually a form of corneal neuropathy that results when corneal nerves are severed by surgery or inflamed after viral infection.

Allergic conjunctivitis is an inflammation of the conjunctiva resulting from hypersensitivity to one or more allergens. It may be acute, intermittent, or chronic. It occurs seasonally, that is, at only certain time of the year, or it occurs perennially, that is, chronically throughout the year. Symptoms of seasonal and perennial allergic conjunctivitis include, in addition to inflammation of the conjunctiva, lacrimation, tearing, conjunctival vascular dilation, itching, papillary hyperlasia, chemosis, eyelid edema, and discharge from the eye. The discharge may form a crust over the eyes after a night's sleep.

Atopic keratoconjunctivitis is a chronic, severe form of allergic conjunctivitis that often leads to visual impairment. Symptoms include itching, burning, pain, redness, foreign body sensation, light sensitivity and blurry vision. There is often a discharge, especially on awakening from a night's sleep; the discharge may be stringy, ropy, and mucoid. The lower conjunctiva is often more prominently affected than the upper conjunctiva. The conjunctiva may range from pale, edematous, and featureless to having the characteristics of advanced disease, including papillary hypertrophy, subepithelial fibrosis, formix foreshortening, trichiasis, entropion, and madurosis. In some patients the disease progresses to punctate epithelial erosions, corneal neovascularization, and other features of keratopathy which may impair vision. There is typically goblet cell proliferation in the conjunctiva, epithelial pseudotubular formation, and an increased number of degranulating eosinophils and mast cells in the epithelium. CD25+T lymphocytes, macrophages, and dendritic cells (HLA-DR.sup.+, HLA-CD1+) are significantly elevated in the substantia propria.

Like atopic keratoconjunctivitis, vernal keratoconjunctivitis is a severe form of allergic conjunctivitis, but it tends to affect the upper conjunctiva more prominently than the lower. It occurs in two forms. In the palpebral form, square, hard, flattened, closely packed papillae are present; in the bulbar (limbal) form, the circumcorneal conjunctiva becomes hypertrophied and grayish. Both forms are often accompanied by a mucoid discharge. Corneal epithelium loss may occur, accompanied by pain and photophobia, as may central corneal plaques and Trantas' dots.

Administration

Formulations of the invention are administered to the subconjunctival space. As used herein, the "subconjunctival space" refers to any of the following: (1) the potential space between the bulbar conjunctiva and Tenon's capsule and extending from the limbus to the formix; (2) the potential space between the palpebral conjunctiva and the tarsus and extending from the eye lid margin (mucocutaneous junction of the eyelid) to the formix; and (3) the potential space just beneath the formiceal conjunctiva at the junctional bay or formix. The subconjunctival space is therefore the potential space just beneath the conjunctiva from the limbus, around the formix, to the eye lid margin.

Figure 5:
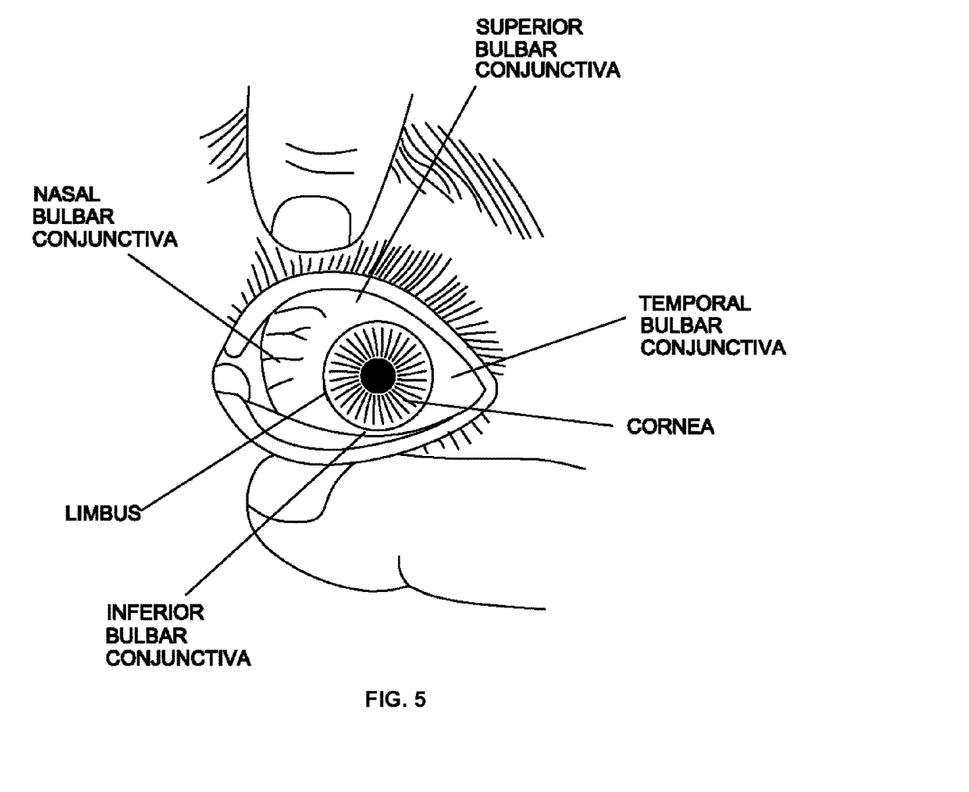
FIG. 5 shows the front of the eye and the different quadrants of the conjunctiva relative to the limbus and cornea.
Figure 6:
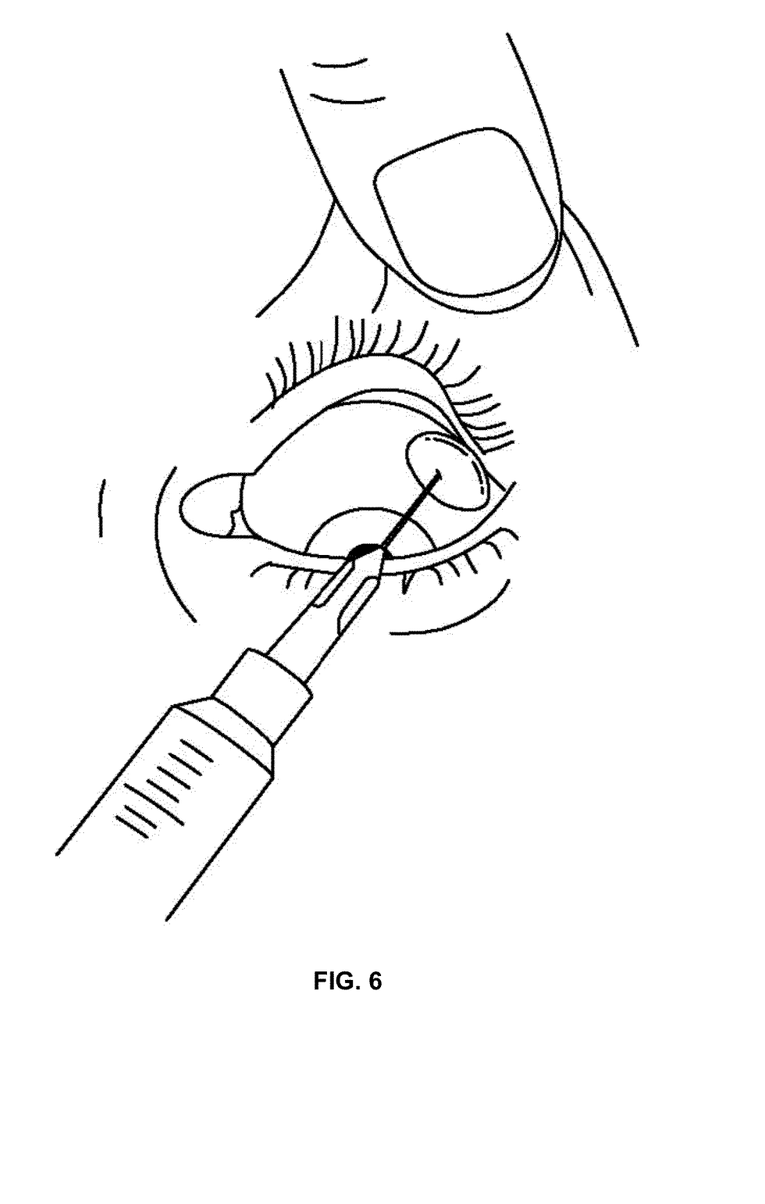
FIG. 6 illustrates injection of a steroid compound into the superotemporal quadrant of the subconjunctival space of the eye. The patient looks down while the thumb of one hand is used to gently retract the upper lid. The syringe containing the steroid-containing composition is placed tangential to the globe and inserted through the bulbar conjunctiva thereby introducing the needle into the subconjunctival space.
Figure 7:
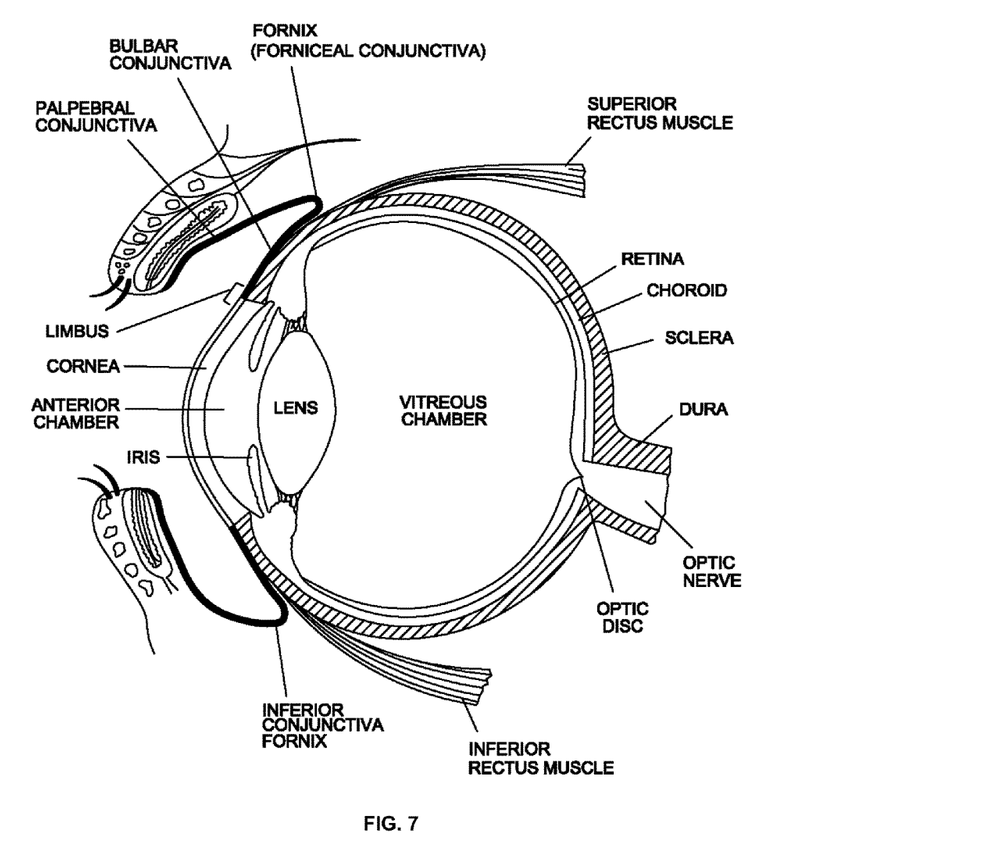
FIG. 7 shows a cross section of the eye and the location of the three zones of the conjunctiva (heavy black line)—palpebral, formiceal, and bulbar—relative to other anatomical regions in the eye.

Referring to FIG. 5, the subconjunctival space around the eye can be divided into four quadrants: the superior, nasal, inferior, and temporal. These quadrants may be further subdivided into sub-quadrants, such as the superotemporal, superonasal, inferior nasal, and inferior temporal, and so on. Hence, the formulations of the invention may be administered, for example, to the superotemporal quadrant of the bulbar subconjunctival space, or to any one or more of the inferior, superior, nasal, or temporal quadrants of the bulbar, palpepral, or formiceal subconjunctival spaces, or to the superotemporal, superonasal, inferior temporal, or inferior nasal bulbar, palpepral, or formiceal subconjunctival spaces (FIGS. 6 and 7). Therefore, unless further delimited, administration into the "subconjunctival space" of the eye refers to administration into any of the bulbar, palpebral, and/or formiceal subconjunctival spaces in the eye in any one or more of the four quadrants of the eye (superior, nasal, temporal, and inferior), or any one or more of the possible sub-quadrants of the eye, including the supertemporal, superonasal, inferior temporal, or inferior nasal regions of the bulbar, palpepral, or formiceal subconjunctival spaces.

In one embodiment, administration of the formulations of the invention excludes their topical delivery (such as by eye drops) to the surface of the eye, or more specifically the cornea, since the subconjunctival space does not include any region or space immediately over, under, or within the cornea. In another embodiment, administration to the subconjunctival space further excludes a delivery method that penetrates or perforates Tenon's capsule or the sclera, that penetrates or extends through the sclera into the vitreous body, or that is delivered beneath the sclera. The "subconjunctival space", as used herein, is not equivalent to the "sub-tenon space." Tenon's capsule is a thin, fibrous, somewhat elastic membrane, beneath the conjunctiva, that envelopes the eyeball from the edge of the cornea (limbus) to the optic nerve. It attaches loosely to the sclera. Thus, the sub-tenon space is between Tenon's capsule and the sclera. Sub-tenon administration of a composition to an eye generally involves elevating both the conjunctiva and Tenons' capsule using forceps and then introducing the composition into the space between the sclera and Tenon's capsule. A needle and syringe may be used to pierce Tenon's capsule and inject the composition into the sub-tenon space.

In one embodiment, the device for administering the formulations of the invention to the subconjunctival space of an eye is a syringe equipped with a needle or a cannula. The needle or cannula used to inject a ophthalmic composition into the subconjunctival space of an eye can be a 20 gauge or higher gauge needle or cannula. The needle or cannula may have a blunt or beveled end. In preferred embodiments, the gauge of the needle or cannula used in the method is a 25 gauge or higher needle or cannula, or is specifically a 22, 23, 24, 25, 26, 27, 28, 29, 30, 31, 32, 33, or 34 gauge needle or cannula.

In one embodiment of the present method for treating an ocular surface inflammation or inflammation of the ocular surface adnexa in a subject in need thereof, a formulation of the invention is injected into the subconjunctival space of the eye (i.e., administered) according to the following procedure. With the subject facing the practitioner, the practitioner uses a thumb (or device such as forceps) to retract the upper or lower eye lid, depending on whether injection into the subconjunctival space is to take place in the superior (e.g., superotemporal) or inferior quadrants, respectively. See FIG. 2, for example. With the other hand, the practitioner positions the needle (attached to a syringe containing the composition) tangential to the eye globe with the needle bevel facing toward the globe (i.e., with the needle bevel facing down). In certain instances, it may be preferable to orient the needle with the bevel facing up (i.e., away from the globe). Keeping the needle tangential to the globe and using a gentle stabbing motion, the practitioner then directs the needle posteriorly and just beneath the conjunctiva to introduce the needle into the subconjunctival space. The desired volume of composition is then injected into the subconjunctival space. Depending on the volume injected, the composition may appear as an elevation or small bulge in the conjunctiva. The needle is then withdrawn. Pressure may then be applied to the eye with a gauze pad to help distribute and diffuse the composition and stem possible bleeding.

In certain embodiments, the same procedure may be used to introduce anesthetic into the subconjunctival space of the eye prior to injecting the formulation of the invention. The anesthetic solution may appear as an elevation or bulge in the conjunctiva. If this procedure is followed, and once the anesthetic has taken effect, the composition is then injected into the elevated portion of the conjunctiva but at a site other than that used to inject the anesthetic. In some embodiments, an additional dose of formulation of the invention may be injected into the nasal and/or inferior (e.g., the inferior formiceal) subconjunctival space using the same procedure outlined above.

Alternatively, an ocular anesthetic may be applied topically to one or each eye prior to injection of the composition into the subconjunctival space of the eye. Analgesic agents may also be administered following subconjunctival administration of the composition. Analgesic agents include triple antibiotic ointment or atropine drops or ointment.

EXAMPLES

The invention is further illustrated by the following examples.

The inventors' work suggests that biodegradable implants containing cyclosporin A, when delivered through a 22 gauge needle, do not deliver sufficient drug over a sufficient period of time to effectively treat those conditions of the eye for which topical cyclosporin A is prescribed or known to be effective in treating.

The inventors prepared the following formulations, and injected them into rabbit eyes.

|  | Cornea | Bulbar Conjunctiva | Lacrimal Gland |
|---|---|---|---|
| 5% CsA R100 (5 mg) | 131 | 287 | 128 |
| 5% CsA RB (5 mg) | 357 | 29.2 | 79.0 |
| 5% CsA HA (5 mg) | 360 | 6720 (possible outlier or error) | 132 |
| 1% CsA HA (1 mg) | 167 | 192 | 24.9 |
| 10% CsA CMC (10 mg) | TBD | TBD | TBD |
| 10% CsA HPMC (10 mg) | TBD | TBD | TBD |
| 10% CsA PVP (10 mg) | TBD | TBD | TBD |
| 10% CsA HA (10 mg) | In progress | In progress | In progress |
| P1L (0.5 mg) | 9.37 | 31700 (possible outlier or error) | 1.51 |
| P1H (1.5 mg) | 54.4 | 143 (possible outlier or error) | 11.4 |
| P2L (0.5 mg) | 10.9 | 80.4 | 1.92 |
| P2H (1.5 mg) | 15.9 | 201 | 3.47 |
| P3L (0.5 mg) | 1.37 | NC | 2.09 |
| P3H (1.5 mg) | 5.98 | 0.801 | 2.73 |
| RESTASIS (0.015 mg) | 1360 | 237 | 13.8 |

What is claimed is:

1. A method of treating a condition selected from the group consisting of dry eye, blepharitis, meibomian gland disease, impaired corneal sensitivity, allergic conjunctivitis, atopic keratoconjunctivitis, vernal keratoconjunctivitis, and ptyregia, the method comprising the step of administering to a subconjunctival space of an eye of a patient having the condition a formulation comprising cyclosporin A form 2 and a hydrogel, the hydrogel selected from the group consisting of hyaluronic acid, hydroxypropyl cellulose, hydroxypropylmethyl cellulose, hydroxyethylcellulose, polyvinyl pyrolidone, carboxymethylcellulose hydroxyethyl cellulose, and polyvinylpyrrolidone.

2. The method of claim 1, comprising administering the formulation through a needle of a gauge no larger than 22.

* * * * *